US008178099B2

(12) United States Patent
Ellies

(10) Patent No.: US 8,178,099 B2
(45) Date of Patent: May 15, 2012

(54) METHODS OF ALTERING BONE GROWTH BY ADMINISTRATION OF SOST OR WISE ANTAGONIST OR AGONIST

(75) Inventor: Debra L. Ellies, Kansas City, MO (US)

(73) Assignee: OsteoGeneX Inc. KS (US)

( * ) Notice: Subject to any disclaimer, the term of this patent is extended or adjusted under 35 U.S.C. 154(b) by 164 days.

(21) Appl. No.: 11/962,522

(22) Filed: Dec. 21, 2007

(65) Prior Publication Data

US 2008/0160060 A1   Jul. 3, 2008

Related U.S. Application Data

(60) Provisional application No. 60/882,642, filed on Dec. 29, 2006.

(51) Int. Cl.
*A61K 39/395* (2006.01)
*A61K 9/00* (2006.01)
*A61K 38/23* (2006.01)
*A61K 31/59* (2006.01)

(52) U.S. Cl. ............... 424/145.1; 424/158.1; 424/178.1; 424/484; 514/11.9; 514/167

(58) Field of Classification Search .................. None
See application file for complete search history.

(56) References Cited

U.S. PATENT DOCUMENTS

| | | | |
|---|---|---|---|
| 4,631,211 A | 12/1986 | Houghten | |
| 4,816,567 A | 3/1989 | Cabilly et al. | |
| 4,935,496 A | 6/1990 | Kudo et al. | |
| 4,946,778 A | 8/1990 | Ladner et al. | |
| 5,010,175 A | 4/1991 | Rutter et al. | |
| 5,118,667 A * | 6/1992 | Adams et al. | 514/12 |
| 5,298,852 A | 3/1994 | Meyer | |
| 5,324,819 A | 6/1994 | Oppermann et al. | |
| 5,344,654 A | 9/1994 | Rieger et al. | |
| 5,468,845 A | 11/1995 | Oppermann et al. | |
| 5,502,167 A | 3/1996 | Waldmann et al. | |
| 5,530,101 A | 6/1996 | Queen et al. | |
| 5,558,864 A | 9/1996 | Bendig et al. | |
| 5,565,332 A | 10/1996 | Hoogenboom et al. | |
| 5,585,089 A | 12/1996 | Queen et al. | |
| 5,639,641 A | 6/1997 | Pedersen et al. | |
| 5,656,593 A | 8/1997 | Kuberasampath et al. | |
| 5,693,493 A | 12/1997 | Robinson et al. | |
| 5,693,761 A | 12/1997 | Queen et al. | |
| 5,693,762 A | 12/1997 | Queen et al. | |
| 5,698,417 A | 12/1997 | Robinson et al. | |
| 5,705,154 A | 1/1998 | Dalie et al. | |
| 5,733,743 A | 3/1998 | Johnson et al. | |
| 5,750,078 A | 5/1998 | Shitara et al. | |
| 5,770,403 A | 6/1998 | Dalie et al. | |
| 5,939,039 A | 8/1999 | Sapieszko et al. | |
| 5,989,334 A * | 11/1999 | Dry | 106/677 |
| 6,190,880 B1 | 2/2001 | Israel et al. | |
| 6,395,511 B1 | 5/2002 | Brunkow et al. | |
| 6,426,332 B1 | 7/2002 | Rueger et al. | |
| 6,489,445 B1 | 12/2002 | Brunkow et al. | |
| 6,949,251 B2 | 9/2005 | Dalal et al. | |
| 7,156,880 B2 * | 1/2007 | Evans et al. | 623/23.51 |
| 7,189,263 B2 | 3/2007 | Erbe et al. | |
| 7,332,276 B2 * | 2/2008 | Sutherland et al. | 435/6 |
| 7,572,899 B2 * | 8/2009 | Brunkow et al. | 536/23.1 |
| 2002/0169122 A1 | 11/2002 | Majumdar et al. | |
| 2002/0187104 A1 | 12/2002 | Li et al. | |
| 2003/0229041 A1 * | 12/2003 | Sutherland et al. | 514/44 |
| 2004/0009535 A1 | 1/2004 | Brunkow et al. | |
| 2004/0023356 A1 | 2/2004 | Krumlauf et al. | |
| 2004/0235728 A1 | 11/2004 | Stoch et al. | |
| 2005/0256047 A1 | 11/2005 | Vignery et al. | |
| 2006/0094656 A1 | 5/2006 | Vignery et al. | |
| 2006/0165799 A1 | 7/2006 | Kim et al. | |
| 2006/0177475 A1 | 8/2006 | Rueger et al. | |
| 2006/0178752 A1 | 8/2006 | Yaccarino, III | |
| 2006/0188542 A1 | 8/2006 | Bobyn et al. | |
| 2006/0188544 A1 | 8/2006 | Saito | |
| 2006/0198863 A1 | 9/2006 | DePaula | |
| 2006/0204542 A1 | 9/2006 | Zhang et al. | |

(Continued)

FOREIGN PATENT DOCUMENTS

WO             94/06416           3/1994

(Continued)

OTHER PUBLICATIONS

Abatangelo et al. The frequent mutation Gly/Asp in CDR1H may determine a cross-reactive idiotype in anti-I cold agglutinins. Clin Exp Immunol. Apr. 1996;104(1):185-90.*
Berzofsky JA. Intrinsic and extrinsic factors in protein antigenic structure. Science. Sep. 6, 1985;229(4717):932-40.*
Deregt et al. Mapping of a type 1-specific and a type-common epitope on the E2 (gp53) protein of bovine viral diarrhea virus with neutralization escape mutants. Virus Res. Jan. 1998;53(1):81-90.*
Kelly et al. Intercellular adhesion molecule-1-deficient mice are protected against ischemic renal injury. J Clin Invest. Feb. 15, 1996;97(4):1056-63.*
McGuinness et al. Class 1 outer membrane protein of Neisseria meningitidis: epitope analysis of the antigenic diversity between strains, implications for subtype definition and molecular epidemiology. Mol Microbiol. Feb. 1993;7(4):505-14.*

(Continued)

*Primary Examiner* — David Romeo
(74) *Attorney, Agent, or Firm* — Fitzpatrick, Cella, Harper & Scinto

(57) ABSTRACT

The present invention provides a method of promoting local bone growth by administering a therapeutic amount of a Sost antagonist to a mammalian patient in need thereof. Preferably, the Sost antagonist is an antibody or FAB fragment selectively recognizing any one of SEQ ID NOS: 1-23. The Sost antagonist may be coadministered together or sequentially with a matrix conducive to anchoring new bone growth. Orthopedic and Periodontal devices comprising an implantable portion adapted to be permanently implanted within a mammalian body and bearing an external coating of a Sost antagonist are also disclosed, as it a method of increasing bone density by administering to a mammalian patient a therapeutic amount of a Sost antagonist together with an antiresorptive drug.

27 Claims, No Drawings

U.S. PATENT DOCUMENTS

| | | | |
|---|---|---|---|
| 2006/0252724 | A1 | 11/2006 | Lyons et al. |
| 2006/0293667 | A1 | 12/2006 | Vignery et al. |
| 2007/0172479 | A1 | 7/2007 | Warne et al. |
| 2007/0292444 | A1 | 12/2007 | Krumlauf et al. |
| 2007/0298038 | A1 | 12/2007 | Krumlauf et al. |
| 2008/0051343 | A1 | 2/2008 | Vignery et al. |
| 2008/0057051 | A1 | 3/2008 | Vignery et al. |
| 2009/0130113 | A1 | 5/2009 | Kneissel et al. |

FOREIGN PATENT DOCUMENTS

| | | |
|---|---|---|
| WO | 03/039534 | 5/2003 |
| WO | 03/073991 | 9/2003 |
| WO | 03/106657 | 12/2003 |
| WO | 2005/003158 | 1/2005 |
| WO | 2006/102070 | 9/2006 |
| WO | 2006/119107 | 11/2006 |
| WO | 2008/133722 | 11/2008 |

OTHER PUBLICATIONS

Peerlinck et al. Antifactor VIII antibody inhibiting allogeneic but not autologous factor VIII in patients with mild hemophilia A. Blood. Apr. 1, 1999;93(7):2267-73.*

Sutcliffe et al. Antibodies that react with predetermined sites on proteins. Science. Feb. 11, 1983;219(4585):660-6.*

Warmington et al. Sclerostin monoclonal antibody treatment of osteoporotic rats completely reverses one year of ovariectomy-induced systemic bone loss. Journal of Bone and Mineral Research, (Sep. 2005) vol. 20, No. 9, Suppl. 1, pp. S22.*

Yanagita, "Modulator of bone morphogenic protein activity in the progression of kidney diseases", Kidney Int., vol. 70, No. 6 (2006) 989-93.

Yanagita, et al., "Uterine sensitization-associated gene-1 (USAG-1), a novel antagonist expressed in the kidney, accelerates tubular injury", J. Clin. Invest., vol. 116, No. 1 (2005) 70-9.

Yanagita, "BMP antagonists: their roles in development and involvement in pathophysiology", Cytokine Growth Factor Rev., vol. 16, No. 3 (2005) 309-17.

Yanagita, et al., "USAG-1: a bone morphogenic protein antagonist abundantly expressed in the kidney", Biochem. Biophys. Res. Commun., vol. 316, No. 2 (2004) 490-500.

Ellies, et al., "Bone Density Ligand, Sclerostin, Directly Interacts With LRP5 but not . . . ", Journal of Bone and Mineral Research, vol. 21, No. 11 ((2006) 1738-49.

Poole, et al., "Sclerostin is a delayed secreted product of osteocytes that inhibits bone formation", FASEB Journal, Vol. 19, No. 13 (2005) 1-18.

van Bezooijen, et al., "SOST/sclerostin, an osteocyte-derived negative regulator of bone formation", Cytokine and Growth Factor Reviews, vol. 16, No. 3 (2005) 319-27.

Balemans, et al., "Increased bone density in sclerosteosis is due to the deficiency of a novel secreted protein (SOST)", Human Molecular Genetics, vol. 10, No. 5, (2001) 537-43.

van Bezooijen, et al., "Wnt but Not BMP Signaling Is Involved in the Inhibitory Action of Sclerostin on BMP-Stimulated Bone Formation", Journal of Bone and Mineral Research, vol. 22, No. 1 (2007) 19-28.

Hosking, et al., "Osteoporosis therapy: an example of putting evidence-based medicine into clinical practice", QJM: Monthly Journal of the Association of Physicians, vol. 98, No. 6 (2005) 403-413.

Heaney, "Advances in therapy for osteoporosis", Clinical Medicine & Research, vol. 1, No. 2 (2003) 93-99.

Macdonald, et al., "Emerging therapies in osteoporosis," Clinical Rheumatology, vol. 15, No. 3 (2001) 483-496.

Díez, "Skeletal effects of selective oestrogen receptor modulators (SERMS)", Human Reproduction Update, vol. 6, No. 3 (2000) 255-258.

Khosla, et al., "Treatment options for osteoporosis", Mayo Clinic Proceedings, vol. 70, No. 10 (1995) 978-982.

Black, et.al., The effects of parathyroid hormone and alendronate alone or in combination in post menopausal osteoporosis, New Eng. J. Med., vol. 349, No. 13 (2003) 1207-15.

Finkelstein, The effects of parathyroid hormone, alendronate, or both in men with osteoporosis, New Eng. J. Med., vol. 349, No. 13 (2003) 1216-26.

Lintern, et al., "Characterization of Wise Protein and Its Molecular Mechanism to Interact with both Wnt and BMP Signals", J. Biol. Chem., vol. 284, No. 34 (2009) 23159-68.

Merriam Webster's Medical Desk Dictionary (1986) 376.

Merriam Webster's Medical Desk Dictionary (1986) 375-376.

Merriam Webster's Medical Desk Dictionary (1986) 448.

Padhi, et al., "Single-dose, Placebo-controlled, Randomized Study of AMG 785, a Sclerostin Monoclonal Antibody", J. Bone Min. Res. (2010) prepublication 1-21.

Silverman, Sclerostin, J. Osteoporosis, vol. 2010 (2010) 941419.

* cited by examiner

SEQUENCE LISTING

```
<160> NUMBER OF SEQ ID NOS: 23

<210> SEQ ID NO 1
<211> LENGTH: 11
<212> TYPE: PRT
<213> ORGANISM: Human

<400> SEQUENCE: 1

Asp Thr Gly Thr Asp Arg Ile Glu Val Thr Arg
1               5                   10

<210> SEQ ID NO 2
<211> LENGTH: 14
<212> TYPE: PRT
<213> ORGANISM: Human

<400> SEQUENCE: 2

Glu Asn Asn Lys Thr Met Asn Arg Ala Glu Asn Gly Gly Arg
1               5                   10

<210> SEQ ID NO 3
<211> LENGTH: 16
<212> TYPE: PRT
<213> ORGANISM: Human

<400> SEQUENCE: 3

His Pro Phe Glu Thr Lys Asp Val Ser Glu Tyr Ser Cys Arg Glu Leu
1               5                   10                  15

<210> SEQ ID NO 4
```

-continued

```
<211> LENGTH: 17
<212> TYPE: PRT
<213> ORGANISM: Human

<400> SEQUENCE: 4

Arg Glu Leu His Phe Thr Arg Tyr Val Thr Asp Gly Pro Cys Arg Ser
1               5                   10                  15

Ala

<210> SEQ ID NO 5
<211> LENGTH: 17
<212> TYPE: PRT
<213> ORGANISM: Human

<400> SEQUENCE: 5

Gln Leu Leu Cys Pro Gly Gly Glu Ala Pro Arg Ala Arg Lys Val Arg
1               5                   10                  15

Leu

<210> SEQ ID NO 6
<211> LENGTH: 14
<212> TYPE: PRT
<213> ORGANISM: Canine

<400> SEQUENCE: 6

Glu Asn Asn Lys Thr Met Asn Arg Ala Glu Asn Gly Gly Arg
1               5                   10

<210> SEQ ID NO 7
<211> LENGTH: 14
<212> TYPE: PRT
<213> ORGANISM: Canine

<400> SEQUENCE: 7

His Pro Phe Glu Thr Lys Ser Glu Tyr Ser Cys Arg Glu Leu
1               5                   10

<210> SEQ ID NO 8
<211> LENGTH: 17
<212> TYPE: PRT
<213> ORGANISM: Canine

<400> SEQUENCE: 8

Arg Glu Leu His Phe Thr Arg Tyr Val Thr Asp Gly Pro Cys Arg Ser
1               5                   10                  15

Ala

<210> SEQ ID NO 9
<211> LENGTH: 17
<212> TYPE: PRT
<213> ORGANISM: Canine

<400> SEQUENCE: 9

Arg Val Gln Leu Leu Cys Pro Gly Gly Ala Ala Pro Arg Ala Arg Lys
1               5                   10                  15

Val

<210> SEQ ID NO 10
<211> LENGTH: 14
<212> TYPE: PRT
<213> ORGANISM: Chimpanzee

<400> SEQUENCE: 10
```

```
Glu Asn Asn Lys Thr Met Asn Arg Ala Glu Asn Gly Gly Arg
1               5                   10
```

<210> SEQ ID NO 11
<211> LENGTH: 16
<212> TYPE: PRT
<213> ORGANISM: Chimpanzee

<400> SEQUENCE: 11

```
His Pro Phe Glu Thr Lys Asp Val Ser Glu Tyr Ser Cys Arg Glu Leu
1               5                   10                  15
```

<210> SEQ ID NO 12
<211> LENGTH: 17
<212> TYPE: PRT
<213> ORGANISM: Chimpanzee

<400> SEQUENCE: 12

```
Arg Glu Leu His Phe Thr Arg Tyr Val Thr Asp Gly Pro Cys Arg Ser
1               5                   10                  15

Ala
```

<210> SEQ ID NO 13
<211> LENGTH: 15
<212> TYPE: PRT
<213> ORGANISM: Chimpanzee

<400> SEQUENCE: 13

```
Leu Cys Pro Gly Gly Ala Ala Pro Arg Ala Arg Lys Val Arg Leu
1               5                   10                  15
```

<210> SEQ ID NO 14
<211> LENGTH: 14
<212> TYPE: PRT
<213> ORGANISM: Human

<400> SEQUENCE: 14

```
Ser Ser Asn Ser Thr Leu Asn Gln Ala Arg Asn Gly Gly Arg
1               5                   10
```

<210> SEQ ID NO 15
<211> LENGTH: 16
<212> TYPE: PRT
<213> ORGANISM: Human

<400> SEQUENCE: 15

```
Thr Gly Leu Asp Arg Asn Ser Arg Val Gln Val Gly Cys Arg Glu Leu
1               5                   10                  15
```

<210> SEQ ID NO 16
<211> LENGTH: 16
<212> TYPE: PRT
<213> ORGANISM: Murine

<400> SEQUENCE: 16

```
Thr Gly Leu Asp Arg Asn Thr Arg Val Gln Val Gly Cys Arg Glu Leu
1               5                   10                  15
```

<210> SEQ ID NO 17
<211> LENGTH: 17
<212> TYPE: PRT
<213> ORGANISM: Human

<400> SEQUENCE: 17

```
Arg Glu Leu Arg Ser Thr Lys Tyr Ile Ser Asp Gly Gln Cys Thr Ser
```

```
1               5                   10                  15

Ile

<210> SEQ ID NO 18
<211> LENGTH: 16
<212> TYPE: PRT
<213> ORGANISM: Human

<400> SEQUENCE: 18

Gln Leu Gln Cys Gln Asp Gly Ser Thr Arg Thr Tyr Lys Ile Thr Val
1               5                   10                  15

<210> SEQ ID NO 19
<211> LENGTH: 15
<212> TYPE: PRT
<213> ORGANISM: Human

<400> SEQUENCE: 19

Pro Leu Lys Glu Leu Val Cys Ala Gly Glu Cys Leu Pro Leu Pro
1               5                   10                  15

<210> SEQ ID NO 20
<211> LENGTH: 14
<212> TYPE: PRT
<213> ORGANISM: Human

<400> SEQUENCE: 20

Gly Thr Lys Tyr Trp Ser Arg Arg Ser Ser Gln Glu Trp Arg
1               5                   10

<210> SEQ ID NO 21
<211> LENGTH: 14
<212> TYPE: PRT
<213> ORGANISM: Human

<400> SEQUENCE: 21

Cys Lys Cys Lys Arg Tyr Thr Arg Gln His Asn Glu Ser Ser
1               5                   10

<210> SEQ ID NO 22
<211> LENGTH: 213
<212> TYPE: PRT
<213> ORGANISM: Human

<400> SEQUENCE: 22

Met Gln Leu Pro Leu Ala Leu Cys Leu Val Cys Leu Leu Val His Thr
1               5                   10                  15

Ala Phe Arg Val Val Glu Gly Gln Gly Trp Gln Ala Phe Lys Asn Asp
                20                  25                  30

Ala Thr Glu Ile Ile Pro Glu Leu Gly Glu Tyr Pro Glu Pro Pro Pro
            35                  40                  45

Glu Leu Glu Asn Asn Lys Thr Met Asn Arg Ala Glu Asn Gly Gly Arg
        50                  55                  60

Pro Pro His His Pro Phe Glu Thr Lys Asp Val Ser Glu Tyr Ser Cys
65                  70                  75                  80

Arg Glu Leu His Phe Thr Arg Tyr Val Thr Asp Gly Pro Cys Arg Ser
                85                  90                  95

Ala Lys Pro Val Thr Glu Leu Val Cys Ser Gly Gln Cys Gly Pro Ala
            100                 105                 110

Arg Leu Leu Pro Asn Ala Ile Gly Arg Gly Lys Trp Trp Arg Pro Ser
        115                 120                 125
```

-continued

```
Gly Pro Asp Phe Arg Cys Ile Pro Asp Arg Tyr Arg Ala Gln Arg Val
    130                 135                 140

Gln Leu Leu Cys Pro Gly Gly Glu Ala Pro Arg Ala Arg Lys Val Arg
145                 150                 155                 160

Leu Val Ala Ser Cys Lys Cys Lys Arg Leu Thr Arg Phe His Asn Gln
                165                 170                 175

Ser Glu Leu Lys Asp Phe Gly Thr Glu Ala Ala Arg Pro Gln Lys Gly
                180                 185                 190

Arg Lys Pro Arg Pro Arg Ala Arg Ser Ala Lys Ala Asn Gln Ala Glu
        195                 200                 205

Leu Glu Asn Ala Tyr
    210

<210> SEQ ID NO 23
<211> LENGTH: 15
<212> TYPE: PRT
<213> ORGANISM: Human

<400> SEQUENCE: 23

Pro Val Thr Glu Leu Val Cys Ser Gly Gln Cys Gly Pro Ala Arg
1               5                   10                  15
```

METHODS OF ALTERING BONE GROWTH BY ADMINISTRATION OF SOST OR WISE ANTAGONIST OR AGONIST

BACKGROUND OF THE INVENTION

1. Field of the Invention

The present invention relates to methods of altering bone growth. In particular, the present invention relates to promoting local bone growth by administering therapeutic amounts of a Sclerostin (hereinafter sometimes "Sost") or Wise antagonist with or without an osteoconductive scaffold to a mammal. In a different embodiment, the present invention relates to implantable medical devices comprising Sost or Wise antagonists or agonists. In a different embodiment, the present invention relates to promoting new bone by systemic administration of a Sost or Wise antagonist in combination with an antiresorptive agent. In another embodiment, the present invention relates to methods of reducing bone both systemically and locally by administering a therapeutic amount of a Sost or Wise agonist to a mammal. In a still further embodiment, the present invention relates to a method of protecting a mammalian kidney from any chemical injury or glomuleronephritis by administering a Wise or Sost antagonist.

2. Brief Description of the Background Art

It is well-understood that bone formation is indicated for treatment of a wide variety of disparate disorders in mammals including simple aging, bone degeneration and osteoporosis, fracture healing, fusion or arthrodesis, osteogenesis imperfecta, etc., as well as for successful installation of various medical orthopedic and periodontal implants such as screws, rods, titanium cage for spinal fusion, hip joints, knee joint, ankle joints, shoulder joints, dental plates and rods, etc. Contrariwise, it is also understood that more rarely disorders appear in mammals wherein bone is overproduced such as in: heterotopic ossification or osteosarcoma treatment, to prevent progression or reduce spinal stenosis of osseous origin such as osteophyte or ossification of the posterior longitudinal ligament, to prevent spontaneous fusion or orthrodesis with joint or disc arthroplasty, to prevent or treat spontaneous spinal fusion such as diffuse idiopathic skeletal hyperostosis and ankylosing spondylitis, preventing ossification or calcification of ligaments, tendons or joint capsules, treating heterotopic bone formation, preventing systemic hyperostosis resulting from metabolic bone disease, and Paget's disease. For these indications and others it is desired to reduce or inhibit such overproduction when possible.

Increasing bone mineralization to treat conditions characterized at least in part by increased bone resorption, such as osteopenia, bone fractures, osteoporosis, arthritis, tumor metastases, Paget's disease and other metabolic bone disorders, using cathepsin K inhibitors and TGF-beta binding proteins, etc., are well-known as shown by US patent application No. 20040235728 to Selwyn Aubrey Stoch, published Nov. 25, 2004, and Mary E. Brunkow et al U.S. Pat. No. 6,489,445 and US patent application publication 20040009535, published Jan. 15, 2004. In the Brunkow '535 and '445 publication, the TGF-beta binding proteins include Sost polypeptide (full length and short peptide) antibodies that interfere with the interaction between the TGF-beta binding protein sclerostin and a TGF-beta superfamily member, particularly a bone morphogenic protein. All of the diseases named above are due to a systemic loss of bone mineral and thus the administration of the antibody therapeutic is for systemic (whole body) increase in bone mineral density.

In the Brunkow '445 and '535 patent, the binding proteins preferably bind specifically to at least one human bone morphogenic protein (BMP) among BMP-5 and BMP-6.

U.S. Pat. No. 6,395,511 to Brunkow, et al. teaches a novel family of human TGF-beta binding proteins and nucleic acids encoding them. The protein binds to at least human bone morphogenic protein-5 and human bone morphogenic protein-6.

Sclerosteosis is a progressive sclerosing bone dysplasia. Sclerostin (the Sost gene) was originally identified as the sclerosteosis-causing gene. Sclerostin was intensely expressed in developing bones of mouse embryos. Punctuated expression of sclerostin was localized on the surfaces of both intramembranously forming skull bones and endochondrally forming long bones. The physiological role of sclerostin remains to be elucidated. However, it is known that loss of function mutations in Sost cause a rare bone dysplasia characterized by skeletal overgrowth.

In-San Kim's US patent application No. 20060165799, published Jul. 27, 2006, teaches a bone-filling composition for stimulating bone-forming and bone-consolidation comprising biocompatible calcium sulfate and viscous biopolymers. The composition is intended to be administered easily into the missing part of injured bone without diffusing to surrounding organs.

In Ronald S. Sapieszko's U.S. Pat. No. 5,939,039, issued in 1999 teaches the processes to yield unique calcium phosphate precursor minerals that can be used to form a self-setting cement or paste. Once placed in the body, these calcium phosphate cements (CPC) will be resorbed and remodeled (converted) to bone.

For example, calcium phosphate particles prepared in accordance with the '039 patent can be used in any of the orthopaedic or dental procedures known for the use of calcium phosphate; the procedures of bone filling defect repair, oncological defect filling, craniomaxillofacial void filling and reconstruction, dental extraction site filling.

US patent application No. 20060198863 to Carl Alexander DePaula, published Sep. 7, 2006, relates to a formable ceramic composition for filling bone defects. The composition comprises ceramic beta tricalcium phosphate particles having a particle size from about 40 microns to 500 microns admixed with a hydrogel carrier containing citric acid buffer. The composition has a pH between 7.0 to 7.8 and the hydrogel component of the carrier ranges from about 1.0 to 5.0% of the composition.

Wise and SOST are understood to be closely related family members (Ellies et al, JBMR 2006 November; 21(11):1738-49.). Those of ordinary skill are aware that the Wise null mutant mouse exhibits a bone phenotype (Keynote presentation at the 2005 American Society of Bone Mineral Research meeting in Nashville, Tenn. State of the Art lectures, an embryonic source of skeletal tissue. Patterning Craniofacial Development; by Robb Krumlauf, Ph.D., Stowers Institute for Medical Research, Kansas City, Mo., USA US patent application No. 20050256047 to Vignery published Nov. 17, 2005 shows induction of bone formation by mechanically inducing an increase in osteoblast activity and elevating systemic blood concentration of a bone anabolic agent, including optionally elevating systemic blood concentration of an antiresorptive agent.

Finally, Yanagita, *Modulator of bone morphogenic protein activity in the progression of kidney diseases, Kidney Int.*, Vol. 70, No. 6 (2006) 989-93 shows Usag-1 (also known as "Wise") protects the kidney from cisplatin insult due to BMB inhibition. See also Yanagita, *Uterine sensitization-associated gene*-1 (*USAG*-1), *a novel antagonist expressed in the* kidney, accelerates tubular injury, J. Clin. Invest., Vol. 116, No. 1 (2005) 70-9, Yanagita, *BMP antagonists: their roles in development and involvement in pathophysiology, Cytokine Growth Factor Rev.*, Vol 16, No. 3 (2005) 309-17, and Yanagita, *USAG-1: a bone morphogenic protein antagonist abundantly expressed in the kidney, Biochem. Biophys. Res. Commun.*, Vol. 316, No. 2 (2004) 490-500 and

SUMMARY OF THE INVENTION

It is an object of the present invention to provide a method of promoting local bone growth, comprising the steps of administering locally a therapeutic amount of a Sost antagonist to a mammalian patient in need thereof.

It is an object of the present invention to provide a method of promoting local bone growth, comprising the steps of administering locally a therapeutic amount of a Wise antagonist to a mammalian patient in need thereof.

It is an object of the present invention to provide a method of promoting local bone growth, comprising the steps of administering locally a therapeutic amount of a Sost antagonist in conjunction with an osteoconductive biocompatible calcium salt scaffold to a mammalian patient in need thereof.

It is an object of the present invention to provide a method of promoting local bone growth, comprising the steps of administering locally a therapeutic amount of a Wise antagonist in conjunction with an osteoconductive biocompatible calcium salt scaffold to a mammalian patient in need thereof.

It is a further object of the present invention to provide a medical orthopedic or periodontal device, comprising a structural support, wherein an implantable portion of said structural support is adapted to be permanently implanted within a mammalian body, said implanted structure support being at least partially retained in said body by local bone growth, said structural support bearing an at least a partial external coating of a Sost antagonist with or without an osteoconductive biocompatible scaffold.

It is a further object of the present invention to provide a medical orthopedic or periodontal device, comprising a structural support, wherein an implantable portion of said structural support is adapted to be permanently implanted within a mammalian body, said implanted structure support being at least partially retained in said body by local bone growth, said structural support bearing an at least a partial external coating of a Wise antagonist with or without an osteoconductive biocompatible scaffold.

It is a still further object of the present invention to provide a method of increasing bone density both systemically (whole body) and locally, comprising the steps of administering, to a mammalian patient in need thereof, a therapeutic amount of a Sost antagonist together with an antiresorptive drug.

It is a still further object of the present invention to provide a method of increasing bone density both systemically (whole body) and locally, comprising the steps of administering, to a mammalian patient in need thereof, a therapeutic amount of a Wise antagonist together with an antiresorptive drug.

It is a still further object of the present invention to provide a method of reducing bone both locally and systemically (whole body), comprising the steps of administering a therapeutic amount of a Sost agonist to a mammalian patient in need thereof.

It is a still further object of the present invention to provide a method of reducing bone both locally and systemically (whole body), comprising the steps of administering a therapeutic amount of a Wise agonist to a mammalian patient in need thereof.

Yet another object of the present invention lies in a method of protecting a mammalian kidney from chemical injury which results in for example glomuleronephritis, comprising administering systemically or locally, to a patient in need thereof, a therapeutic amount of a SOST or Wise antagonist.

These objects and others are provided by novel processes utilizing administration of Sost antagonists or agonists to mammalian patients. In particular, Sost antibody antagonists or agonists administered locally with or without an osteoconductive matrix or in conjunction with an antiresorptive agent. Alternatively, a Sost antibody antagonists administered systemically (whole body) in conjunction with an antiresorptive. Desirable Sost antagonists function through LRP5 or LRP6, or comprises an antibody or FAB fragment recognizing any one of SEQ ID NOS: 1-23.

The above features and advantages are provided by the present invention which utilizes either a Sost or Wise antagonist or a Sost or Wise agonist to provide bone growth or depletion, respectively.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As disclosed herein, proteins, particularly antibodies, muteins, nucleic acid aptamers, and peptide that antagonize specific binding of SOST or WISE (Usag-1/ectodin/sostdc1) to their natural receptors may serve as "binding agents" and "SOST antagonists or agonists" or "WISE antagonists or agonists" of the present invention.

Those of ordinary skill in this art are able to determine the appropriate "therapeutically effective amount" for administering such agonists and antagonists, as well as methods and schedules for such administration The phrase "specifically (or selectively) binds" or when referring to an antibody interaction, "specifically (or selectively) immunoreactive with," refers to a binding reaction between two molecules that is at least two times the background and more typically more than 10 to 100 times background molecular associations under physiological conditions. When using one or more detectable binding agents that are proteins, specific binding is determinative of the presence of the protein, in a heterogeneous population of proteins and other biologics. Thus, under designated immunoassay conditions, the specified antibodies bind to a particular protein sequence, thereby identifying its presence.

Specific binding to an antibody under such conditions requires an antibody that is selected for its specificity for a particular protein For example, antibodies raised against a particular protein, polymorphic variants, alleles, orthologs, and conservatively modified variants, or splice variants, or portions thereof, can be selected to obtain only those polyclonal antibodies that are specifically immunoreactive with SOST, WISE or an LRP, preferably an LRP5 or LRP6 protein and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity). Methods for determining whether two molecules specifically interact are disclosed herein, and methods of determining binding affinity and specificity are well known in the art (see, for example, Harlow and Lane, Antibodies: A laboratory manual (Cold Spring Harbor Laboratory Press, 1988); Friefelder, "Physical Biochemistry: Applications to biochemistry and molecular biology" (W.H. Freeman and Co. 1976)).

Furthermore, Sost or Wise can interfere with the specific binding of a receptor and its ligand by various mechanism, including, for example, by binding to the ligand binding site, thereby interfering with ligand binding; by binding to a site other than the ligand binding site of the receptor, but sterically interfering with ligand binding to the receptor; by binding the receptor and causing a conformational or other change in the receptor, which interferes with binding of the ligand; or by other mechanisms. Similarly, the agent can bind to or otherwise interact with the ligand to interfere with its specifically interacting with the receptor. For purposes of the methods disclosed herein, an understanding of the mechanism by which the interference occurs is not required and no mechanism of action is proposed. A Wise or Sost binding agent, such as an anti-Wise or anti-Sost antibody, or antigen binding fragment thereof, is characterized by having specific binding activity ($K_a$) of at least about $10^5$ $M^{-1}$, $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, Ann. NY Acad. Sci. 51: 660-72, 1949).

The term "antibody" as used herein encompasses naturally occurring antibodies as well as non-naturally occurring antibodies, including, for example, single chain antibodies, chimeric, bifunctional and humanized antibodies, as well as antigen-binding fragments thereof, (e.g., Fab', F(ab')2, Fab, Fv and rIgG). See also, Pierce Catalog and Handbook, 1994-1995 (Pierce Chemical Co., Rockford, Ill.). See also, e.g., Kuby, J., Immunology, 3rd Ed., W.H. Freeman & Co., New York (1998). Such non-naturally occurring antibodies can be constructed using solid phase peptide synthesis, can be produced recombinantly or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

The term "antibody" includes both polyclonal and monoclonal antibodies. The term also includes genetically engineered forms such as chimeric antibodies (e.g., humanized murine antibodies) and heteroconjugate antibodies (e.g., bispecific antibodies). The term also refers to recombinant single chain Fv fragments (scFv). The term antibody also includes bivalent or bispecific molecules, diabodies, triabodies, and tetrabodies. Bivalent and bispecific molecules are described in, e.g., Kostelny et al. (1992) J Immunol 148:1547, Pack and Pluckthun (1992) Biochemistry 31:1579, Hollinger et al., 1993, supra, Gruber et al. (1994) J Immunol:5368, Zhu et al. (1997) Protein Sci 6:781, Hu et al. (1996) Cancer Res. 56:3055, Adams et al. (1993) Cancer Res. 53:4026, and McCartney, et al. (1995) Protein Eng. 8:301.

A "humanized antibody" is an immunoglobulin molecule that contains minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, a humanized antibody will comprise substantially all of at least one, and typically two, variable domains, in which all or substantially all of the CDR regions correspond to those of a non-human immunoglobulin and all or substantially all of the framework (FR) regions are those of a human immunoglobulin consensus sequence. The humanized antibody optimally also will comprise at least a portion of an immunoglobulin constant region (Fc), typically that of a human immunoglobulin (Jones et al., Nature 321:522-525 (1986); Riechmann et al., Nature 332: 323-329 (1988); and Presta, Curr. Op. Struct. Biol. 2:593-596 (1992)). Humanization can be essentially performed following the method of Winter and co-workers (Jones et al., Nature 321:522-525 (1986); Riechmann et al., Nature 332:323-327 (1988); Verhoeyen et al., Science 239:1534-1536 (1988)), by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar naturally occurring and non-naturally occurring amino acids are well known in the art. Such conservatively modified variants are in addition to and do not exclude polymorphic variants, interspecies homologs, and alleles of the invention. Typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M); Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

"Homologous," in relation to two or more peptides, refers to two or more sequences or subsequences that have a specified percentage of amino acid residues that are the same (i.e., about 60% identity, preferably 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI or the like). The definition also includes sequences that have deletions and/or additions, as well as those that have substitutions, as well as naturally occurring, e.g., polymorphic or allelic variants, and man-made variants. As described below, the preferred algorithms can account for gaps and the like. Preferably, identity exists over a region that is at least about 25 amino acids in length, or more preferably over a region that is 50-100 amino acids in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of one of the number of contiguous positions selected from the group consisting typically of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

Preferred examples of algorithms that are suitable for determining percent sequence identity and sequence similarity include the BLAST and BLAST 2.0 algorithms, which are described in Altschul et al., Nuc. Acids Res. 25:3389-3402 (1977) and Altschul et al., J. Mol. Biol. 215:403-410 (1990). BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a peptide is considered similar to a reference sequence if the smallest sum probability in a comparison of the test peptide to the reference peptide is less than about 0.2, more preferably less than about 0.01, and most preferably less than about 0.001. Log values may be large negative numbers, e.g., 5, 10, 20, 30, 40, 40, 70, 90, 110, 150, 170, etc.

DETAILED DESCRIPTION OF THE INVENTION

The present invention is directed to methods for promoting local bone deposition in mammals using materials that antagonize Sost proteins. Suitable antagonists may be provided by blocking antibodies. Antibodies include those that specifically bind to any of Sost agonist proteins according to SEQ ID NOS: 1-23 or homologs that are >75% identity and more preferable antibodies are monoclonal and/or humanized antibodies. It is similarly desirable that the antagonist operates through LRP5 or LRP6. The antagonist may be coadministered or serially administered with an antiresorptive drug if desired to increase or hasten bone formation. For example, the antiresorptive drug may be a bisphosphonate (i.e. fosamax, actonel), a PTH or analog (i.e. Forteo), calcitonin or analog (i.e. Miacalcic), Vitamin D or analog, SERM or analog (i.e. Evista), These blocking Sost-recognizing antibodies may be made readily by those of ordinary skill in this art by conventional techniques. Preferably, these antibodies will be FAB fragments or monoclonal antibodies, and more preferably, the FAB fragments or monoclonal antibodies will be humanized. Suitable humanized monoclonal antibodies have been created by Amgen, for example. Stowers Institute also provides suitable blocking antibodies designated 4G10, 4B9 and 6E6. Another suitable blocking antibody is 1A12 commercially available from Abcam.

The present invention is directed to methods for reducing bone in mammals using materials that agonize Sost or Wise proteins, by administering to a mammal a peptide that recognizes any of SEQ ID NOS: 1-23. Peptides for treating systemic (whole body) low bone mass diseases are taught in Applicant's U.S. patent application Ser. No. 11/508,701 (U.S. publication No. 20070292444) and in Applicant's US patent application publication No. 20040023356. All subject matter of both the Ser. Nos. 11/508,701 and 11/613,658 (U.S. publication No. 20070298038) applications and the 20040023356 publication is hereby incorporated by reference.

The present invention is directed to methods for protecting mammalian kidneys from any chemical injury that causes renal damage, for example glomuleronephritis, by administering to a mammal a Sost or Wise antagonist. Such subject matter is disclosed in the Ser. Nos. 11/508,701 and 11/613,658 applications and the 20040023356 publication, incorporated by reference.

Other aspects of the present invention are directed towards medical implants. Such medical devices and implants include, for example, the osteogenic devices and methods of using the same for repairing endochondral bone and osteochondral defects taught in US patent application publication No. 20060177475 to David Rueger et al, published Aug. 10, 2006, as well as in issued US Patent and published application U.S. Pat. No. 6,190,880, 20020169122, 20020187104, 20060252724, 20070172479, U.S. Pat. Nos. 5,344,654, 5,324,819, 5,468,845, 6,949,251, 6,426,332 and 5,656,593, the subject matter of which is hereby incorporated by reference.

These medical devices generally provide a structural support having an implantable portion preferentially adapted to mechanically engage bone and/or cartilage as taught, for instance, in US patent application publication No. 20060178752 to Joseph Vaccarino III, et al, published Aug. 10, 2006, the subject matter of which is hereby incorporated by reference. These bone implants desirably comprise an active agent on at least a portion thereof. As shown by US patent application publication No. 20060188542 to John Dennis Bobyn, et al, published Aug. 24, 2006, the subject matter of which is hereby incorporated by reference, the active agent is preferably formulated to be locally deliverable to bone proximate the implant in sustained-release or in at least a two-phased release scheme. In the latter, a first phase rapidly releases a first quantity of the active agent, and the second and subsequent phases gradually release a second quantity of the active agent, whereby bone formation stimulated by the active agent is modulated.

Medical devices such as bone implants feature implantable portions bearing Sost antagonists foster quicker and more complete bone formation in situ. The implantable portion of the medical device may be desirable at least partially or totally covered or impregnated with a Sost antagonist. It has believed to be helpful to produce the implantable portion of the medical device from a matrix material in which bone can be formed, to increase permanently retaining the same. This is thought to be desirable for materials such as teeth and artificial bone graft sections, and the like. Alternatively, when the implantable sections are load bearing and formed, e.g., of stainless steel, these implantable sections are desirable formed with a Sost antagonist coating. In that event, it is desirable to also provide a separate matrix material conducive to forming new bone growth.

Suitable matrixes include those comprising composite biomaterials having a sponge-like structure such as those containing, e.g., phosphophoryn and/or collagen as taught in Takashi Saito's US patent application publication No. 20060188544, published Aug. 24, 2006, the subject matter of which is hereby incorporated by reference. Such coatings include, for example, the single and multilayer coatings taught in US patent application publication No. 20060204542 to Zongtao Zhang et al, published Sep. 14, 2006, as well as those in U.S. Pat. Nos. 6,949,251, 5,298,852, 5,939,039, and 7,189,263 and may be made by conventional methods including the methods taught therein, the subject matter of which is hereby incorporated by reference.

Usag-1 (Wise) may be functioning through the Wnt pathway for its role in renal protection. For this reason and others, a therapeutic amount of a Wise antagonist may be administered to a mammalian patient in need thereof so as to protect a kidney from renal damage for example glomuleronephritis. In particular, it is especially preferred to administer such Wise or Sost blocking antibodies so as to protect the mammalian kidney from external insult engendered from disease or chemicals, such as toxins or drug therapy.

The present invention also contemplates agents that antagonize binding of SOST and/or WISE to its native receptor(s) ("SOST antagonist"). SOST antagonist include a peptidomimetic, which is an organic molecule that mimics the structure of a peptide; or a peptoid such as a vinylogous peptoid.

The present invention also contemplates agents that agonize binding of SOST and/or WISE to its native receptor(s) ("SOST agonists). SOST or Wise agonists include a peptidomimetic, which is an organic molecule that mimics the structure of a peptide; or a peptoid such as a vinylogous peptoid.

Preferred embodiments of the present invention include SOST antagonists that are preferably SOST antibodies, WISE antibodies or LRP antibodies, although the invention also contemplates inhibitory peptides and small molecular inhibitors as described above. Antibodies of the invention are preferably chimeric, more preferably humanized antibodies, ideally monoclonal antibodies preferably raised against murine proteins, most preferably murine SOST.

SOST, WISE, or LRP antagonist antibodies, including anti-SOST antibodies, may be raised using as an immunogen, such as a substantially purified full length protein, such as murine SOST, but may also be a SOST, WISE or LRP protein of human, mouse or other mammalian origin. The immunogen may be prepared from natural sources or produced recombinantly, or a peptide portion of a protein, which can include a portion of the cystiene knot domain, for example, a synthetic peptide. A non-immunogenic peptide may be made immunogenic by coupling the hapten to a carrier molecule such bovine serum albumin (BSA) or keyhole limpet hemocyanin (KLH), or by expressing the peptide portion as a fusion protein. Various other carrier molecules and methods for coupling a hapten to a carrier molecule are well known in the art and described, for example, by Harlow and Lane (supra, 1988).

Particularly useful antibodies for performing methods of the invention are monoclonal antibodies that that specifically bind to LRP molecules, WISE or, most preferably, SOST. Such antibodies are particularly useful where they bind SOST with at least an order of magnitude greater affinity than they bind another protein. Methods for creating chimeric antibodies, including humanized antibodies, is discussed in greater detail below.

1. Production of Recombinant Antibody

Methods for producing both monoclonal and polyclonal antibodies from identified proteins or peptides are well known in the art. In order to prepare recombinant chimeric and humanized antibodies that may function as SOST antagonists of the present invention, the nucleic acid encoding non-human antibodies must first be isolated. This is typically done by immunizing an animal, for example a mouse, with prepared Sost or Wise or an antigenic peptide derived therefrom. Typically mice are immunized twice intraperitoneally with approximately 50 micrograms of protein antibody per mouse. Sera from immunized mice can be tested for antibody activity by immunohistology or immunocytology on any host system expressing such polypeptide and by ELISA with the expressed polypeptide. For immunohistology, active antibodies of the present invention can be identified using a biotin-conjugated anti-mouse immunoglobulin followed by avidin-peroxidase and a chromogenic peroxidase substrate. Preparations of such reagents are commercially available; for example, from Zymad Corp., San Francisco, Calif. Mice whose sera contain detectable active antibodies according to the invention can be sacrificed three days later and their spleens removed for fusion and hybridoma production. Positive supernatants of such hybridomas can be identified using the assays common to those of skill in the art, for example, Western blot analysis.

The nucleic acids encoding the desired antibody chains can then be isolated by, for example, using hybridoma mRNA or splenic mRNA as a template for PCR amplification of the heavy and light chain genes [Huse, et al., Science 246:1276 (1989)]. Nucleic acids for producing both antibodies and intrabodies can be derived from murine monoclonal hybridomas using this technique [Richardson J. H., et al., Proc Natl Acad Sci USA 92:3137-3141 (1995); Biocca S., et al., Biochem and Biophys Res Comm, 197:422-427 (1993) Mhashilkar, A. M., et al., EMBO J 14:1542-1551 (1995)]. These hybridomas provide a reliable source of well-characterized reagents for the construction of antibodies and are particularly useful once their epitope reactivity and affinity has been characterized. Isolation of nucleic acids from isolated cells is discussed further in Clackson, T., et al., Nature 352:624-628 (1991) (spleen) and Portolano, S., et al., supra; Barbas, C. F., et al., supra; Marks, J. D., et al., supra; Barbas, C. F., et al., Proc Natl Acad Sci USA 88:7978-7982 (1991) (human peripheral blood lymphocytes). Humanized antibodies optimally include at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

A number of methods have been described to produce recombinant antibodies, both chimeric and humanized. Controlled rearrangement of antibody domains joined through protein disulfide bonds to form chimeric antibodies may be utilized (Konieczny et al., Haematologia, 14(1):95-99, 1981). Recombinant DNA technology can also be used to construct gene fusions between DNA sequences encoding mouse antibody variable light and heavy chain domains and human antibody light and heavy chain constant domains (Morrison et al., Proc. Natl. Acad. Sci. USA, 81(21):6851-6855, 1984.).

DNA sequences encoding the antigen binding portions or complementarity determining regions (CDR's) of murine monoclonal antibodies may be grafted by molecular means into the DNA sequences encoding the frameworks of human antibody heavy and light chains (Jones et al., Nature, 321 (6069):522-525, 1986; Riechmann et al., Nature, 332(6162): 323-327, 1988.). The expressed recombinant products are called "reshaped" or humanized antibodies, and comprise the framework of a human antibody light or heavy chain and the antigen recognition portions, CDR's, of a murine monoclonal antibody.

Other methods for producing humanized antibodies are described in U.S. Pat. Nos. 5,693,762; 5,693,761; 5,585,089; 5,639,641; 5,565,332; 5,733,743; 5,750,078; 5,502,167; 5,705,154; 5,770,403; 5,698,417; 5,693,493; 5,558,864; 4,935,496; 4,816,567; and 5,530,101, each incorporated herein by reference in their entirety.

Techniques described for the production of single chain antibodies (U.S. Pat. No. 4,946,778, which is incorporated by reference) can be adapted to produce single chain humanized antibodies to Sost or Wise.

2. Purification of Recombinant Antibody

Affinity purification of an antibody pool or sera provides a practitioner with a more uniform reagent. Methods for enriching antibody granulation inhibitors using antibody affinity matrices to form an affinity column are well known in the art and available commercially (AntibodyShop, c/o Statens Serum Institut, Artillerivej 5, Bldg. P2, DK-2300 Copenhagen S). Briefly, an antibody affinity matrix is attached to an affinity support (see e.g.; CNBR Sepharose (R), Pharmacia Biotech). A mixture comprising antibodies is then passed over the affinity matrix, to which the antibodies bind. Bound antibodies are released by techniques common to those familiar with the art, yielding a concentrated antibody pool. The enriched antibody pool can then be used for further immunological studies, some of which are described herein by way of example.

Another approach uses recombinant bacteriophage to produce large libraries. Using the "phage method" (Scott and Smith, Science 249:386-390, 1990; Cwirla, et al, Proc. Natl. Acad. Sci., 87:6378-6382, 1990; Devlin et al., Science, 49:404-406, 1990), very large libraries can be constructed (106-108 chemical entities). A second approach uses primarily chemical methods, of which the Geysen method (Geysen et al., Molecular Immunology 23:709-715, 1986; Geysen et al. J. Immunologic Method 102:259-274, 1987; and the method of Fodor et al. (Science 251:767-773, 1991) are examples Furka et al. (14th International Congress of Biochemistry, Volume #5, Abstract FR:013, 1988; Furka, Int. J. Peptide Protein Res. 37:487-493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

3. Identification of Sost Antagonists

The present invention provides methods for identifying diagnostic and therapeutic SOST antagonists. Several exemplary methods for identifying such antagonists are described herein, including cell-based and in vitro techniques. A general method of identifying SOST antagonists involves evaluating the effects of antagonist candidates on bone deposition under controlled conditions. Preferably bone deposition is determined using micro-CT techniques on live animals. Preferred animals include rodents, more preferred are primates. Femur and vertebrae bones are particularly useful subjects for such study.

Briefly, the test animal is treated with a predetermined dose of a SOST antagonist candidate. A control animal is treated with a control solution, preferably a non-irritating buffer solution or other carrier.

It also has been found that successful implantation of the osteogenic factors for endochondral bone formation requires association of the proteins with a suitable carrier material capable of maintaining the proteins at an in vivo site of application. The carrier should be biocompatible, in vivo biodegradable and porous enough to allow cell infiltration.

The proteins of this invention, including fragments thereof, also may be used to raise monoclonal or polyclonal antibodies capable of binding specifically to an epitope of Sost, Wise, or LRP. These antibodies may be used, for example, in Sost or Wise antagonists or agonists purification protocols.

The Sost or Wise antagonists or agonists are useful in clinical applications in conjunction with a suitable delivery or support system (matrix). As disclosed herein, the matrix may be combined with Sost or Wise antagonists or agonists to induce endochondral bone formation reliably and reproducibly in a mammalian body. The matrix is made up of particles of porous materials. The pores must be of a dimension to permit progenitor cell migration into the matrix and subsequent differentiation and proliferation. The particle size should be within the range of 70 um-850 um, preferably 70 um-420 um, most preferably 150 um-420 um. It may be fabricated by close packing particulate material into a shape spanning the bone defect, or by otherwise structuring as desired a material that is biocompatible, and preferably biodegradable in vivo to serve as a "temporary scaffold" and substratum for recruitment of migratory progenitor cells, and as a base for their subsequent anchoring and proliferation. Useful matrix materials comprise, for example, collagen; homopolymers or copolymers of glycolic acid, lactic acid, and butyric acid, including derivatives thereof; and ceramics, such as hydroxyapatite, tricalcium phosphate and other calcium phosphates. Combinations of these matrix materials also may be useful.

When the SOST antagonist candidate is delivered in a carrier, the control solution is ideally the carrier absent the SOST antagonist candidate. Multiple doses of the SOST antagonist candidate may be applied to the test animal, preferably following a predetermined schedule of dosing. The dosing schedule may be over a period of days, more preferably over a period of weeks.

Once the dosing schedule has been completed, both test and control animals are examined to determine the level of bone deposition present. This may be accomplished by any suitable method, but is preferably performed on live animals using x-ray equipment. Methods for micro-CT examination of bones in animals are well known in the art. A SOST antagonist candidate suitable for use as a SOST antagonist is identified by noting significant bone deposition in the test animal when compared to the control animal. Ideally bone deposition in the test bone(s) of the test animal should be at least 10%, more preferably 20%, most preferably 30% or 40% or more bone deposition than is present in the same bones of the control animal. Where necessary, levels of bone deposition may be calculated by determining the volume of bone deposition present in each animal. Calculations may be performed by constructing a 3-dimensional image of the bone deposition and calculating the volume from the image with the aid of e.g., histomorphometry.

In an exemplary embodiment, localized injection in situ of a SOST antagonist candidate, for example a monoclonal antibody described herein, may be made into a test animal, with a control animal receiving an equal volume of control solution without the SOST antagonist candidate. Identical dosing should be done on a weekly basis for four weeks. Suitable dosage will depend on the nature of the particular SOST antagonist candidate being tested. By way of example, in dosing it should be noted that systemic injection, either intravenously, subcutaneously or intramuscularly, may also be used. For systemic injection of a SOST antagonist candidate or a SOST antagonist or agonist, dosage should be about 5 mg/kg, preferably more preferably about 15 mg/kg, advantageously about 50 mg/kg, more advantageously about 100 mg/kg, acceptably about 200 mg/kg. dosing performed by nebulized inhalation, eye drops, or oral ingestion should be at an amount sufficient to produce blood levels of the SOST antagonist candidate similar to those reached using systemic injection. The amount of SOST antagonist candidate that must be delivered by nebulized inhalation, eye drops, or oral ingestion to attain these levels is dependent upon the nature of the inhibitor sed and can be determined by routine experimentation. It is expected that, for systemic injection of the monoclonal antibody SOST antagonist candidates described herein, therapeutic levels of the antibody may be detected in the blood one week after delivery of a 15 mg/kg dose.

SOST antagonists may also be identified using a process known as computer, or molecular modeling, which allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. rediction of what the molecule-compound interaction will be when small changes are made in one or both requires molecular mechanics software and computationally intensive computers, usually coupled with user-friendly, menu-driven interfaces between the molecular design program and the user.

An example of the molecular modelling system described generally above consists of the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et. al., Acta Pharmaceutica Fennica 97, 159-166 (1988); Ripka, New Scientist 54-57 (Jun. 16, 1988); McKinaly and Rossmann, Annu. Rev. Pharmacol. Toxiciol. 29, 111-122 (1989); Perry and Davies, OSAR: Ouantitative Structure-Activity Relationships in Drug Design pp. 189-193 (Alan R. Liss, Inc. 1989); Lewis and Dean, Proc. R. Soc. Lond. 236, 25-140 and 141-162 (1989); and, with respect to a model receptor for nucleic acid components, Askew, et al., J. Am. Chem. Soc. 111, 1082-1090 (1989). Askew et al. constructed a new molecular shape which permitted both hydrogen bonding and aromatic stacking forces to act simultaneously. Askew et al. used Kemp's triacid (Kemp et al., J. Org. Chem. 46:5140-5143 (1981)) in which a U-shaped (diaxial) relationship exists between any two carboxyl functions. Conversion of the triacid to the imide acid chloride gave an acylating agent that could be attached via amide or ester linkages to practically any available aromatic surface. The resulting structure featured an aromatic plane that could be roughly parallel to that of the atoms in the imide function; hydrogen bonding and stacking forces converged from perpendicular directions to provide a microenvironment complimentary to adenine derivatives.

Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of RNA, once that region is identified.

4. Screening Compound Libraries

Whether identified from existing SOST antagonists or from molecular modelling techniques, SOST antagonists generally must be modified further to enhance their therapeutic usefulness. This is typically done by creating large libraries of compounds related to the SOST antagonist, or compounds synthesized randomly, based around a core structure. In order to efficiently screen large and/or diverse libraries of SOST antagonist candidates, a high throughput screening method is necessary to at least decrease the number of candidate compounds to be screened using the assays described above. High throughput screening methods involve providing a combinatorial chemical or peptide library containing a large number of potential therapeutic compounds (potential modulator or ligand compounds). Such "combinatorial chemical libraries" or "candidate libraries" are then screened in one or more assays, as described below, to identify those library members (particular chemical species or subclasses) that are able to promote bone deposition. The compounds thus identified can serve as conventional "lead compounds" or can themselves be used as potential or actual therapeutics.

Accordingly, the present invention provides methods for high throughput screening of SOST antagonists candidates. The initial steps of these methods allow for the efficient and rapid identification of combinatorial library members that have a high probability of being SOST antagonists. These initial steps take advantage of the observation that SOST antagonists are also LRP or SOST binding agents. Any method that determines the ability of a member of the library, termed a binding candidate, to specifically bind to SOST, WISE or an LRP protein is suitable for this initial high throughput screening. For example, competitive and non-competitive ELISA-type assays known to one of ordinary skill in the art may be utilized.

Binding candidates that are found to bind SOST, WISE or an LRP protein with acceptable specificity, e.g., with a $K_a$ for SOST, WISE or an LRP protein of at least about $10^5$ $M^{-1}$, $10^6$ $M^{-1}$ or greater, preferably $10^7 M^{-1}$ or greater, more preferably $10^8$ $M^{-1}$ or greater, and most preferably $10^9$ $M^{-1}$ or greater, are SOST antagonist candidates and are screened further, as described above, to determine their ability to promote bone deposition.

5. Therapeutic Applications

Individuals to be treated using methods of the present invention may be any mammal, for example local increase in bone may be used for fracture healing, fusion (arthrodesis), orthopedic reconstruction, and periodontal repair. Systemic increase in bone would be for treatment of low bone mass, i.e. osteoporosis. Bone reduction would be used to treat unwanted heterotopic bone formation, ossification of longitudinal ligament, ossification during cervical stenosis, or osteosarcoma. Such individuals include a dog, cat, horse, cow, or goat, particularly a commercially important animal or a domesticated animal, more particularly a human.

In therapeutic use SOST antagonists generally will be in the form of a pharmaceutical composition containing the antagonist and a pharmaceutically acceptable carrier. Pharmaceutically acceptable carriers are well known in the art and include aqueous solutions such as physiologically buffered saline or other buffers or solvents or vehicles such as glycols, glycerol, oils such as olive oil or injectable organic esters. The selection of a pharmaceutically acceptable carrier will depend, in part, on the chemical nature of the SOST antagonist, for example, whether the SOST antagonist is an antibody, a peptide or a nonpeptide.

A pharmaceutically acceptable carrier may include physiologically acceptable compounds that act, for example, to stabilize the SOST antagonist or increase its absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the SOST antagonist and on its particular physio-chemical characteristics.

Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

The pharmaceutical compositions of the present invention may be prepared for administration by a variety of different routes. In general, the type of carrier is selected based on the mode of administration. Pharmaceutical compositions may be formulated for any appropriate manner of administration, including, for example, topical, oral, nasal, intrathecal, rectal, vaginal, sublingual or parenteral administration, including subcutaneous, intravenous, intramuscular, intrastemal, intracavernous, intrameatal, or intraurethral injection or infusion. A pharmaceutical composition (e.g., for oral administration or delivery by injection) may be in the form of a liquid (e.g., an elixir, syrup, solution, emulsion or suspension). A liquid pharmaceutical composition may include, for example, one or more of the following: sterile diluents such as water for injection, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers such as acetates, citrates or phosphates and agents for the adjustment of tonicity such as sodium chloride or dextrose. A parenteral preparation can be enclosed in ampoules, disposable syringes or multiple dose vials made of glass or plastic. The use of physiological saline is preferred, and an injectable pharmaceutical composition is preferably sterile.

The methods of the present invention include application of SOST antagonists in cocktails including other medicaments, for example, antibiotics, fungicides, and anti-inflammatory agents. Alternatively, the methods may comprise sequential dosing of an afflicted individual with a SOST antagonist and one or more additional medicaments to optimize a treatment regime. In such optimized regimes, the medicaments, including the granulation inhibitor may be applied in any sequence and in any combination.

The SOST, Wise, or LRP antagonists or agonists of the present invention may also be included in slow release formulations for prolonged treatment following a single dose. In one embodiment, the formulation is prepared in the form of microspheres. The microspheres may be prepared as a homogenous matrix of a SOST antagonist with a biodegradable controlled release material, with optional additional medicaments as the treatment requires. The microspheres are preferably prepared in sizes suitable for infiltration and/or injection, and injected systemically, or directly at the site of treatment.

The formulations of the invention are also suitable for administration in all body spaces/cavities, including but not limited to pleura, peritoneum, cranium, mediastinum, pericardium, bursae or bursal, epidural, intrathecal, intraocular, intra-articular, intra-discal, intra-medullary, perispinal, etc.

Some slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone. methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

The amount of SOST, Wise, or LRP antagonist or agonists administered to an individual will depend, in part, on the disease and/or extent of injury. Methods for determining an effective amount of an agent to administer for a diagnostic or a therapeutic procedure are well known in the art and include phase I, phase II and phase III clinical trials. Generally, an agent antagonist is administered in a dose of about 0.01 to 200 mg/kg body weight when administered systemically, and at a concentration of approximately 0.1-100 μM when administered directly to a wound site. The total amount of SOST antagonist or agonists can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a particular SOST antagonist required to provide an effective amount to a region or regions of injury depends on many factors including the age and general health of the subject as well as the route of administration, the number of treatments to be administered, and the nature of the SOST antagonist, including whether the SOST antagonist is an antibody, a peptide, or a nonpeptide molecule. In view of these factors, the skilled artisan would adjust the particular dose so as to obtain an effective amount for efficaciously promoting bone deposition for therapeutic purposes.

All publications and patent applications cited in this specification are herein incorporated by reference as if each individual publication or patent application were specifically and individually indicated to be incorporated by reference.

Although the foregoing invention has been described in some detail by way of illustration and example for clarity and understanding, it will be readily apparent to one of ordinary skill in the art in light of the teachings of this invention that certain changes and modifications may be made thereto without departing from the spirit and scope of the appended claims.

What I claim is:

1. A method of promoting local bone growth, comprising the steps of administering a therapeutic amount of a Sclerostin antagonist implanted locally to a mammalian patient in need thereof, wherein said Sclerostin antagonist comprises an antibody or FAB fragment specifically binding a peptide comprising 10 contiguous amino acids of a sequence selected from the group consisting of SEQ ID NOs: 2-13, 22 and 23, and wherein the antibody interferes with Sclerostin's ability to bind to LRP, thereby providing new local bone formation, wherein said Sclerostin antagonist is implanted in said patient while being affixed to a medical device or a matrix material.

2. The method according to claim 1, further comprising the step of administering to said mammalian patient a biocompatible matrix or scaffold conducive to anchoring new bone growth.

3. The method according to claim 2, wherein said biocompatible matrix or scaffold comprises a material selected from the group consisting of an osteo-conducive scaffold containing a calcium salt, calcium sulfate, autograft, hydroxyapatite, demineralized bone, allograft or tricalcium phosphate.

4. A method of promoting bone according to claim 1, further comprising the steps of administering locally to said mammalian patient a BMP recombinant protein.

5. The method according to claim 4, further comprising the step of administering to said mammalian patient a biocompatible matrix or scaffold conducive to anchoring new bone growth.

6. The method according to claim 5, wherein said biocompatible matrix or scaffold comprises a material selected from the group consisting of a scaffold containing a calcium salt, calcium sulfate, autograft, hydroxyapatite, demineralized bone, allograft or tricalcium phosphate.

7. The method according to any one of claims 4-6, wherein said antibody or FAB fragment is a monoclonal antibody.

8. The method according to claim 7, wherein said antibody is a humanized antibody or FAB fragment.

9. The method according to any one of claims 1-6, wherein said Sclerostin antagonist comprises an antibody or FAB fragment specifically binding SEQ ID NO:23.

10. The method according to claim 9, wherein said antibody or FAB fragment is a monoclonal antibody.

11. The method according to claim 10, wherein said antibody is a humanized antibody or FAB fragment.

12. A method of systemically increasing bone density, comprising the steps of administering, to a mammalian patient in need thereof, a therapeutic comprising an effective amount of a Sclerostin antagonist together with an antiresorptive drug, wherein said Sclerostin antagonist comprises an antibody or FAB fragment specifically binding a peptide comprising 10 contiguous amino acids of a sequence selected from the group consisting of SEQ ID NOs: 2-13, 22 and 23, and wherein the antibody interferes with Sclerostin's ability to bind to LRP, thereby systemically increasing bone density.

13. The method according to claim 12, wherein the therapeutic is administered by implantation.

14. The method according to claim 12, wherein said antiresorptive drug is denosumab, a bisphosphonate, a SERM, calcitonin, a calcitonin analog, Vitamin D, a vitamin D analog, or a Rank antagonist.

15. The method according to any one of claims 12 or 13, wherein said antibody or FAB fragment is a monoclonal antibody.

16. The method according to claim 15, wherein said antibody is a humanized antibody or FAB fragment.

17. The method according to claim 16, wherein said antiresorptive drug is denosumab, a bisphosphonate, a SERM, calcitonin, a calcitonin analog, Vitamin D, a vitamin D analog, or a Rank antagonist.

18. The method according to any one of claims 12 or 13, wherein said Sclerostin antagonist comprises an antibody or FAB fragment specifically binding SEQ ID NO: 23.

19. The method according to claim 18, wherein said antibody or FAB fragment is a monoclonal antibody.

20. The method according to claim 19, wherein said antibody is a humanized antibody or FAB fragment.

21. The method according to claim 20, wherein said antiresorptive drug is denosumab, a bisphosphonate, a SERM, calcitonin, a calcitonin analog, Vitamin D, a vitamin D analog, or a Rank antagonist.

22. The method according to claim 1, wherein said antibody or FAB fragment interferes with Sclerostin's ability to bind to LRP5 or LRP6.

23. The method according to claim 12, wherein said antibody or FAB fragment interferes with Sclerostin's ability to bind to LRP5 or LRP6.

24. The method according to claim 15, wherein said antiresorptive drug is denosumab, a bisphosphonate, a SERM, calcitonin, a calcitonin analog, Vitamin D, a vitamin D analog, or a Rank antagonist.

25. The method according to claim 18, wherein said antiresorptive drug is denosumab, a bisphosphonate, a SERM, calcitonin, a calcitonin analog, Vitamin D, a vitamin D analog, or a Rank antagonist.

26. The method according to claim 19, wherein said antiresorptive drug is denosumab, a bisphosphonate, a SERM, calcitonin, a calcitonin analog, Vitamin D, a vitamin D analog, or a Rank antagonist.

27. The method according to claim 26, wherein said antibody is a humanized antibody or FAB fragment.

* * * * *

UNITED STATES PATENT AND TRADEMARK OFFICE
CERTIFICATE OF CORRECTION

PATENT NO.       : 8,178,099 B2
APPLICATION NO.  : 11/962522
DATED            : May 15, 2012
INVENTOR(S)      : Debra L. Ellies It is certified that error appears in the above-identified patent and that said Letters Patent is hereby corrected as shown below:

TITLE PAGE [57] ABSTRACT:

Line 8, "Periodontal" should read --periodontal--.

COLUMN 1:

Line 34, "joint," should read --joints,--;
Line 56, "No. 20040235728" should read --No. 2004/0235728--; and
Line 58, "200400009535," should read --2004/00009535,--.

COLUMN 2:

Line 19, "No. 20060165799," should read --No. 2006/0165799,--;
Line 26, "In" should be deleted;
Line 38, "No. 20060198863" should read --No. 2006/0198863--; and
Line 56, "No. 20050256047" should read --2005/0256047--.

COLUMN 3:

Line 7, "490-500 and" should read --490-500.--.

COLUMN 4:

Line 9, "agonists administered" should read --agonists may be administered--;
Line 11, "antagonists" should read --antagonist may be--;
Line 14, "comprises" should read --comprise--;
Line 44, "administration" should read --administration.--; and
Line 59, "protein" should read --protein.--.

Signed and Sealed this
Fourteenth Day of August, 2012

David J. Kappos
*Director of the United States Patent and Trademark Office*

CERTIFICATE OF CORRECTION (continued)
U.S. Pat. No. 8,178,099 B2

COLUMN 6:

Line 48, "polymer." should read --polymers.--.

COLUMN 7:

Line 9, "algorithms" should read --algorithm--.

COLUMN 9:

Line 4, "No. 20070292444)" should read --No. 2007/0292444)--;
　　Line 5, "No. 20040023356." should read --No. 2004/0023356.--;
　　Line 7, "No. 20070298038)" should read --No. 2007/0298038)--;
　　Line 8, "20040023356" should read --2004/0023356--;
　　Line 15, "20040023356" should read --2004/0023356--;
　　Line 24, "20020169122, 20020187104," should read --2002/0169122, 2002/0187104,--;
　　Line 25, "20060252724, 20070172479," should read --2006/0252724, 2007/0172479,--;
　　Line 33, "20060178752" should read --2006/0178752--;
　　Line 37, "No. 20060188542" should read --No. 2006/0188542--;
　　Line 47, "feature" should read --featuring--;
　　Line 51, "has" should read --is--;
　　Line 58, "desirable" should read --desirably--;
　　Line 62, "matrixes" should read --matrices--; and
　　Line 66, "20060188544," should read --2006/0188544,--.

COLUMN 10:

Line 2, "No. 20060204502" should read --No. 2006/0204502--;
　　Line 19, "include" should read --includes--;
　　Line 46, "such" should read --such as--;
　　Line 53, "that that" should read --that--; and
　　Line 58, "is" should read --are--.

COLUMN 11:

Line 31, "has" should read --have--.

COLUMN 17:

Line 16, "agnesium" should read --magnesium--.

COLUMN 25:

Line 49, "of promoting bone" should be deleted.

UNITED STATES PATENT AND TRADEMARK OFFICE
CERTIFICATE OF CORRECTION

PATENT NO. : 8,178,099 B2  
APPLICATION NO. : 11/962522  
DATED : May 15, 2012  
INVENTOR(S) : Debra L. Ellies Page 1 of 1

It is certified that error appears in the above-identified patent and that said Letters Patent is hereby corrected as shown below:

COLUMN 26:

Line 62, "SEQ ID NO: 23" should read --SEQ ID NO: 22--.

Signed and Sealed this  
Thirteenth Day of November, 2012

David J. Kappos  
*Director of the United States Patent and Trademark Office*